US010004690B2

United States Patent
Lee et al.

(10) Patent No.: US 10,004,690 B2
(45) Date of Patent: Jun. 26, 2018

(54) ADMINISTRABLE MICROPARTICLES IN VIVO THROUGH MEDICAL CONDUIT

(71) Applicant: UTAH-INHA DDS & ADVANCED THERAPEUTICS RESEARCH CENTER, Incheon (KR)

(72) Inventors: Eunhye Lee, Incheon (KR); Keun Su Kim, Incheon (KR); Don Haeng Lee, Seoul (KR); Young Hwan Park, Gangwon-do (KR)

(73) Assignee: UTAH-INHA DDS & ADVANCED THERAPEUTICS RESEARCH CENTER, Incheon (KR)

( * ) Notice: Subject to any disclaimer, the term of this patent is extended or adjusted under 35 U.S.C. 154(b) by 0 days. days.

(21) Appl. No.: 15/112,797

(22) PCT Filed: Jan. 21, 2015

(86) PCT No.: PCT/KR2015/000630
§ 371 (c)(1),
(2) Date: Jul. 20, 2016

(87) PCT Pub. No.: WO2015/111914
PCT Pub. Date: Jul. 30, 2015

(65) Prior Publication Data
US 2016/0367482 A1      Dec. 22, 2016

(30) Foreign Application Priority Data
Jan. 21, 2014   (KR) .................. 10-2014-0007089

(51) Int. Cl.
| A61K 9/14 | (2006.01) |
| A61K 9/16 | (2006.01) |
| C07K 14/76 | (2006.01) |
| A61K 31/74 | (2006.01) |
| A61K 9/00 | (2006.01) |

(52) U.S. Cl.
CPC .......... *A61K 9/1652* (2013.01); *A61K 9/0019* (2013.01); *A61K 9/14* (2013.01);
(Continued)

(58) Field of Classification Search
CPC ........ A61K 9/14; A61K 9/1658; A61K 31/74; C07K 14/76
See application file for complete search history.

(56) References Cited

U.S. PATENT DOCUMENTS

| 2007/0160543 A1 | 7/2007 | Moller ........................... 424/46 |
| 2011/0125089 A1* | 5/2011 | Senderoff .............. A61K 47/42 |
| | | 604/82 |

FOREIGN PATENT DOCUMENTS

| CN | 101862469 A | 10/2010 |
| CN | 102216381 A | 10/2011 |

(Continued)

OTHER PUBLICATIONS

Hayward et al, Pressure Generated by Syringes:Implications for Hydrodissection and injection of dense connective tissue lesions, Scand J. Rheumatol., 2011, 40(5):379-382.*
(Continued)

*Primary Examiner* — Carlos A Azpuru
(74) *Attorney, Agent, or Firm* — Harness, Dickey & Pierce, P.L.C.

(57) ABSTRACT

The present invention provides administrable microparticles in vivo through a medical conduit, a composition comprising the same, and a manufacturing method therefor. The microparticles of the present invention have an advantage that a clogging phenomenon does not occur for an endoscopic administration through a spray apparatus.

2 Claims, 4 Drawing Sheets

(52) U.S. Cl.
CPC ............ *A61K 9/1658* (2013.01); *A61K 31/74* (2013.01); *C07K 14/76* (2013.01)

(56) References Cited

FOREIGN PATENT DOCUMENTS

| | | | |
|---|---|---|---|
| CN | 103402569 A | 11/2013 | |
| EP | 2 060 253 A1 | 5/2009 | ............... A61K 9/16 |
| JP | 10-306160 A | 11/1998 | |
| JP | 2006-514044 A | 4/2006 | ............... A61K 9/16 |
| JP | 2011-509932 A | 3/2011 | ........... A61K 31/718 |
| JP | 2011-518780 A | 6/2011 | ............. A61K 47/42 |
| JP | 2011-518780 A5 | 5/2012 | ............. A61K 47/42 |
| JP | 2012-527924 | 11/2012 | ............. A61L 15/44 |
| JP | 2011-518780 A5 | 2/2014 | ............. A61K 47/42 |
| KR | 10-2006-0040329 | 5/2006 | ............. A61K 31/74 |
| WO | WO2005115252 | 12/2005 | ............. A61B 17/00 |
| WO | WO 2009/113512 A1 | 9/2009 | |
| WO | 2009132225 A2 | 10/2009 | |
| WO | WO2010136588 A2 | 12/2010 | ............... A61K 9/16 |
| WO | 2012085600 A1 | 6/2012 | |
| WO | WO2013004838 A1 | 1/2013 | ............... A61K 9/16 |
| WO | WO 2006-049463 | 4/2013 | ............. A61K 31/74 |
| WO | WO 2013-053749 | 4/2013 | ............. A61L 24/04 |

OTHER PUBLICATIONS

HarvardApparatus.com. 2017.*
International Search Report (ISR) PCT/KR2015/000630, dated Apr. 28, 2015 published in WO 2015/111914.
ASGE Technology Committee et al., (2012). "Emerging technologies for endoscopic hemostasis gastrointestinal endoscopy". 75(5):933-937.
Cremers H.F.M., et al. (1990) "Albumin-heparin microspheres as carriers for cytostatic agents." *Journal of Controlleo Release*, Elsevier, Amsterdam, NL, vol. 1.11(No. 1-3):167-179. XP023744017,ISSN: 0168-3659, 001: 10.1016/0168-3659(90)90130-L.
Huang, et al. (2014) "Polysaccharide hemostatic system for hemostasis management in colorectal endoscopic mucosal resection." *Digestive Endoscopy*, 26(1):63-68. doi: 10.1111/den.12054.
Ibrahim, MD., et al. (2013) "Endoscopic treatment of acute variceal hemorrhage by using hemostatic powder TC-325: a prospective pilot study." *Gastrointestinal Endoscopy*, 78(5):769-773. http://dx.doi.org/10.1016/j.gie.2013.07.037.
Malafaya, et al. (2007) "Natural-origin polymers as carriers and scaffolds for biomolecules and cell delivery in tissue engineering applications.", *Aovanceo Orug Oelivery Reviews, Elsevier*, Amsterdam, NL, 59(No. 4-5):207-233. XP022110905,ISSN: 0169-409X. 001: 10.1 016/J.AOOR.2007.03.012.
Extended European Search Report, dated May 30, 2017 in European Patent Application No. 15740074.8.
Japanese Office action dated Apr. 17, 2017 in Japan Patent Application No. 2016-547539, with English Translation.
Japanese Office action dated Sep. 22, 2017 in Japan Patent Application No. 2016-547539, with English Translation.
JP Office Action dated Dec. 28, 2017 issue in Japanese Patent Application No. 2016-547539, with English Translation.
Office Action from corresponding Chinese Patent Application No. 201580005237.1 dated Apr. 4, 2018.

* cited by examiner

FIG. 1

40K Dextran

40K Dextran particle (granule)

70K Dextran

70K Dextran particle (granule)

Hydroxyethyl cellulose

Hydroxyethyl cellulose particle (granule)

ADMINISTRABLE MICROPARTICLES IN VIVO THROUGH MEDICAL CONDUIT

CROSS-REFERENCE TO RELATED APPLICATIONS

This application is a national phase application of PCT Application No. PCT/KR2015/000630, filed on Jan. 21, 2015, which claims the benefit and priority to Korean Patent Application No. 10-2014-0007089, filed Jan. 21, 2014. The entire disclosures of the applications identified in this paragraph are incorporated herein by references.

FIELD

The present invention relates to microparticles that are endoscopically administrable in vivo without blockage in a medical conduit, a composition containing the same, and a method for manufacturing the same.

BACKGROUND

Bleeding management is important during surgery. Blood loss may cause innumerable problems in patients, whereas the presence of blood at undesirable locations is harmful to normal tissues or may impede the ability of doctors who check sites of surgery. This bleeding may also be problematic during the minimally invasive surgical procedure (e.g., laparoscopic surgery).

Gastrointestinal bleeding is a frequently encountered clinical problem. At least 80% of gastrointestinal bleeding cases occur in the upper gastrointestinal tract. The upper gastrointestinal tract bleeding refers to a disease in which lesions of esophagus, stomach, and duodenum are bleeding, causing blood vomiting or bloody excrement. The endoscopy can confirm bleeding lesions in 90% or more of gastrointestinal tract bleeding cases, and 40-50% of gastrointestinal tract bleeding cases are known to be caused by stomach ulcer or duodenum bleeding.

In recent years, gastric or colorectal polypectomy or mucosectomy and endoscopic operation for the treatment of early gastric cancer and colorectal cancer have been frequently conducted. During or after these operations, the bleeding causes people to receive emergency surgery or even to die.

Hemostasis using an endoscope has recently been attempted to treat the bleeding during the operation or the gastrointestinal tract bleeding. The hemostasis using an endoscope is conducted by approaching an in vivo inserted endoscopic catheter (medical conduit) to a mucosal lesion in need of hemostasis and then administering and spraying an appropriate hemostatic agent through the catheter. To this end, Hemospray (Cook Medical Inc.) and Endoclot™ are currently used as medical devices.

The devices are designed such that a hemostatic ingredient is administered and sprayed by supplying a predetermined pressure to a medical conduit connected to the devices. However, the conduit may be blocked during the administration of the hemostatic ingredient, and thus the bleeding at the bleeding site may not be stopped on time at the necessary moment.

Therefore, a method for increasing the pressure supplied to the medical conduit may be considered. However, since the conduit has been inserted into the human body, the site of surgery may be affected by the increase of the pressure, and thus it is not possible to increase the pressure to a level at which the conduit blockage can be solved.

Throughout the entire specification, many papers and patent documents are referenced and their citations are represented. The disclosures of cited papers and patent documents are entirely incorporated by reference into the present specification, and the level of the technical field within which the present invention falls and details of the present invention are explained more clearly.

DETAILED DESCRIPTION OF THE INVENTION

Technical Problem

The present inventors have searched and endeavored to develop a preparation causing no conduit blockage when a pharmaceutically active material for bleeding stopping and wound dressing is endoscopically administered in vivo through a medical conduit. As a result, the present inventors have verified that microparticles with a predetermined particle diameter, rather than a powder type, can be administered and sprayed to a target site without causing the blockage in the medical conduit, and then have completed the present invention.

Therefore, an aspect of the present invention is to provide microparticles for in vivo administration through a medical conduit.

Another aspect of the present invention is to provide a composition for in vivo administration through a medical conduit.

Still another aspect of the present invention is to provide a method for manufacturing microparticles that are endoscopically administrable in vivo through a medical conduit with an inner diameter of 1.0-3.5 mm at a pressure of 0.5-2 bar without blockage in the medical conduit.

Still another aspect of the present invention is to provide a method for endoscopically administering polymer microparticles in vivo through a medical conduit with an inner diameter of 1.0-3.5 mm at a pressure of 0.5-2 bar, the polymer microparticles containing a biocompatible and biodegradable polymer and having a particle diameter of 100-350 μm.

Other purposes and advantages of the present invention will become clarified by the following detailed description of the invention, claims, and drawings.

Technical Solution

In accordance with an aspect of the present invention, there are provided microparticles for in vivo administration through a medical conduit, the microparticles being endoscopically administered in vivo through a medical conduit with an inner diameter of 1.0-3.5 mm at a pressure of 0.5-2 bar, wherein the microparticles are polymer microparticles with a particle diameter of 100-350 μm containing a biocompatible and biodegradable polymer.

In accordance with another aspect of the present invention, there is provided a composition for in vivo administration through a medical conduit, the composition containing the microparticles for in vivo administration through a medical conduit.

In accordance with still another aspect of the present invention, there is provided a method for manufacturing microparticles that are endoscopically administrable in vivo through a medical conduit with an inner diameter of 1.0-3.5 mm at a pressure of 0.5-2 bar without causing blockage in the medical conduit, the method including a step of manufacturing polymer microparticles with a particle diameter of 100-350 μm containing a biocompatible and biodegradable polymer.

In accordance with still another aspect of the present invention, there is provided a method for endoscopically administering polymer microparticles in vivo through a medical conduit with an inner diameter of 1.0-3.5 mm at a pressure of 0.5-2 bar, the polymer microparticles containing a biocompatible and biodegradable polymer and having a particle diameter of 100-350 μm.

The present inventors have searched and endeavored to develop a preparation causing no conduit blockage when a pharmaceutically active material for bleeding stopping and wound dressing is endoscopically administered in vivo through a medical conduit. As a result, the present inventors have verified that microparticles with a predetermined particle diameter, rather than a powder type, can be administered and sprayed to a target site without causing the blockage in the medical conduit.

The present invention is based on the findings that when a preparation (e.g., a medical adhesive) is administered into a medical conduit (endoscopic catheter) with a particular inner diameter at a particular pressure, only microparticles with a diameter of 100-350 μm can be administered and sprayed without causing the blockage in the conduit. Therefore, according to the present invention, the microparticles with the above range can be endoscopically administered in vivo through a medical conduit (inner diameter: 1.0-3.5 mm, pressure: 0.5-2 bar) without causing the blockage in the conduit.

As used herein, the term "endoscopically administering" refers to administering to a target site, such as a body tissue, through a medical conduit, such as an in vivo inserted catheter (endoscopic catheter). Endoscopically administering may cover administering using a spray device, which administers a material by supplying pressure to an endoscopic catheter (inserted in vivo) provided in the device according to the operation of a user, for example, Hemospray or Endoclot™. However, the spray device usable for the present invention is not limited to Hemospray and Endoclot™, and any device that can inject a material in vivo through a conduit provided in the device can be used without limitations.

Herein, the medical conduit refers to a conduit with a small diameter, such as a catheter that is normally used in a medical field, and the terms "medical conduit" and "endoscopic catheter" are exchangeably used in the present specification.

The microparticles of the present invention are formed of a biocompatible and biodegradable polymer.

As used herein, the term "polymer microparticles" or "microparticles for in vivo administration" refers to a microsized particle material obtained by an aggregate formed from a polymer having biocompatible and biodegradable characteristics by the strength between particles or through another material (e.g., a excipient). Therefore, the polymer microparticles or microparticles for in vivo administration, regardless of the terminology and expressions, are included within the range of the microparticles intended by the present invention so long as they contain a biocompatible and biodegradable polymer and have a particle material (including a tablet) having a particle diameter of 100-350 μm. Examples of such microparticles may include granular-fine microspheres, porous fine microspheres, and microbeads. In addition, an aggregate or mixture of several homogenous or heterogeneous polymer microparticles with a particle diameter of 100-350 μm may be construed to be included within the range of the polymer microparticles or the microparticles for in vivo administration.

As used herein, the term "biocompatible" refers to an attribute of a material that performs the original functions without bad effects on the living body and can coexist with the living body, which is the property required for a biomedical material. The term "biodegradable" refers to the property of being degradable when exposed to a physiological solution, for example, the property of being degradable by a body fluid or microorganisms in the bodies of mammals including, for example, a human being.

According to an embodiment of the present invention, the biocompatible and biodegradable polymer has a glucose unit as a base unit, and has a glycoside linkage selected from the group consisting of 1,3-, 1,4-, and 1,6-glycoside linkages regardless of the α or β linkage. Examples thereof are α-glucan and β-glucan, and examples of α-glucan may include amylose (α-1,4 linkage), amylopectin (α-1,4 and α-1,6 linkages), glycogen (α-1,4 and α-1,6 linkages), dextran (α-1,6 linkage), and the like, and examples of β-glucan may include cellulose (β-1,4 linkage), laminaran (β-1,3 linkage) of brown algae, lichenan (β-1,3 and β-1,4 linkages) of lichen, and the like, but are not limited thereto.

According to an embodiment of the present invention, the glucose may have —OH, —$NH_2$, —$NHCOCH_3$, or —OOH at the second or fifth carbon atom thereof. Examples of the polymers include dextran, chitosan, hyaluronic acid, alginate, celluloses, starch, and the like.

According to an embodiment of the present invention, examples of the biocompatible and biodegradable polymer include: alginate; chitosan; dextran; serum albumin; dextran sulfate; cellulose; chitin; agarose; amylose; proteoglycan; glycosaminoglycans; collagen; gelatin; pectin; carrageenan; polylysine; pullulan; protamine; amino group-containing PEG, poly(lactic-co-glycolic) acid (PLGA), dendrimer, poly-L-lactide (PLLA) or polyethylenimine (PEI); compounds or polymers including putrescine, cadaverine, and spermidine; proteins; or polypeptides.

According to an embodiment of the present invention, the glycosaminoglycans include hyaluronic acid, chondroitin sulfate, dermatan sulfate, heparan sulfate, heparin, and keratan sulfate.

According to an embodiment of the present invention, the biocompatible and biodegradable polymer has a weight average molecular weight of 1,000-500,000. The molecular weight distribution and average molecular weight of the polymer may be measured by using SDS-PAGE, ion-association chromatography of high-performance liquid chromatography (HPLC), and gel permeation chromatography.

The biocompatible and biodegradable polymer-containing microparticles may be manufactured by a normal method for manufacturing microparticles known in the art. For example, the polymer-containing microparticles may be manufactured by a microfluidic system, an encapsulator, an emulsification method, or the like. In addition, granules, as the microparticles, may be manufactured through granulation using a fluidized bed device (fluidized bed granulator). The device sprays a liquid material toward an upper or lower space from nozzles installed at the top or bottom spray portion in an expansion chamber, thereby generating particles having a similar shape to a dried product that is manufactured by spray drying, and at the same time, these particles are allowed to retain a fluidized state for a predetermined time inside the device, and thus adhesion and coating between particles by the liquid material are repeated, so the particle diameter is slowly increased.

According to an embodiment, the polymer microparticles may further contain a medical excipient in addition to the biocompatible and biodegradable polymer. The excipient is normally used at the time of preparation, and examples thereof include lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, magnesium stearate, mineral oil, and the like, but are not limited thereto. The microparticles of the present invention may further contain, in addition to the above ingredients, a binder, a lubricant, a wetting agent, a colorant, a surfactant, an emulsifier, a preservative, a pH adjusting agent, and the like.

According to the present invention, the pressure applied to the medical conduit may be optionally set within the range of 0.5-2 bar. Through the pressure in the above range, the microparticles with a diameter of 100-350 μm can be administered in vivo through a medical conduit without causing the blockage in the conduit.

According to an embodiment of the present invention, the pressure applied to the medical conduit is 0.5-1.5 bar. The pressure is 0.5-2.0 bar for one particular embodiment, and 0.7-1.1 bar for another particular embodiment.

According to an embodiment of the present invention, the inner diameter of the medical conduit is 1.0-3.5 mm.

The inner diameter of the medical conduit is 1.5-3.2 mm for one particular embodiment, 1.6-3.0 mm for another particular embodiment, 1.7-2.5 mm for still another embodiment, 1.8-2.3 mm for still another embodiment, and 1.9-2.2 mm for still another embodiment.

Advantageous Effects

Features and advantages of the present invention are summarized as follows.

(i) The present invention provides microparticles for in vivo administration through a medical conduit, a composition containing the same, and a method for manufacturing the same.

(ii) The microparticles of the present invention cause no blockage when endoscopically administered through a spray device.

BRIEF DESCRIPTION OF THE DRAWINGS

FIGS. 3 and 4 show actual images of a spray device and a catheter that were used.

Figure 1:
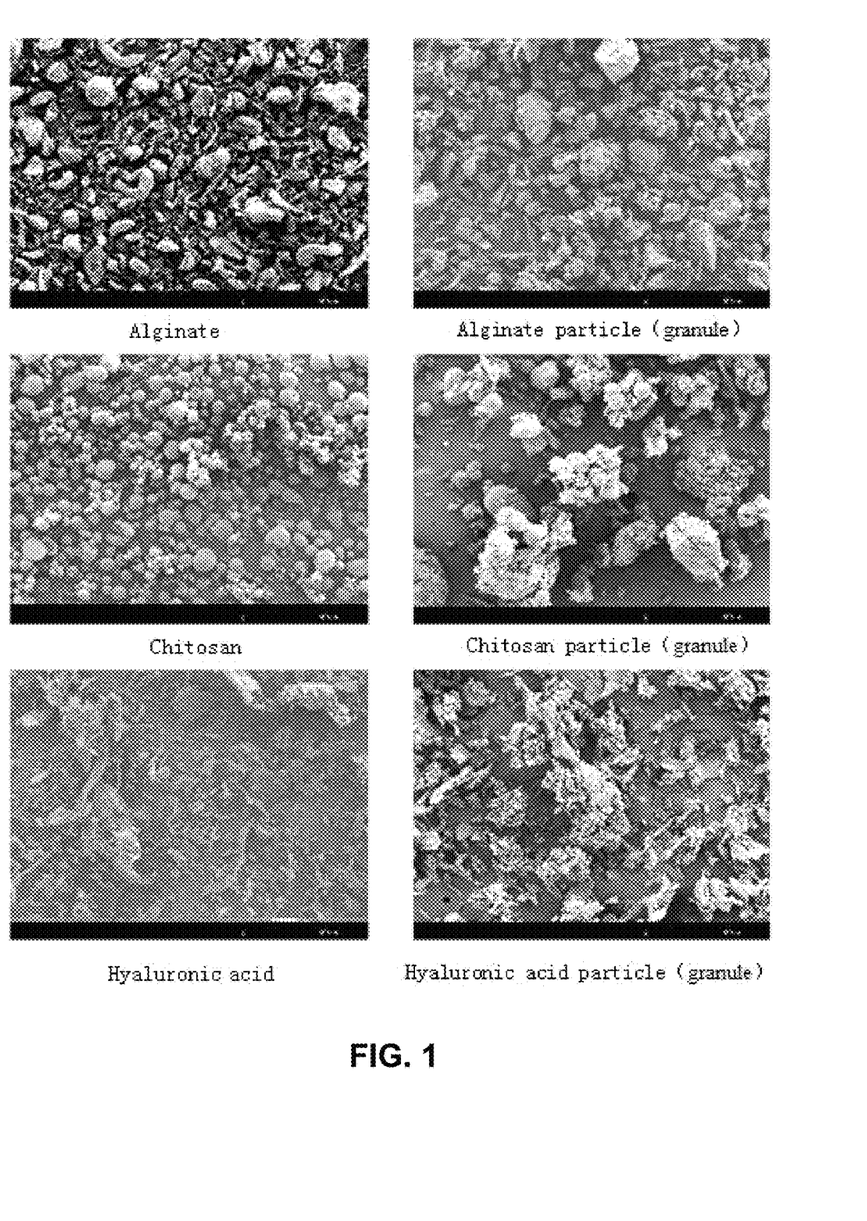
FIG. 1 shows SEM images of microparticles of respective polymers (alginate, chitosan, and hyaluronic acid) manufactured in the example of the present invention.
Figure 2:
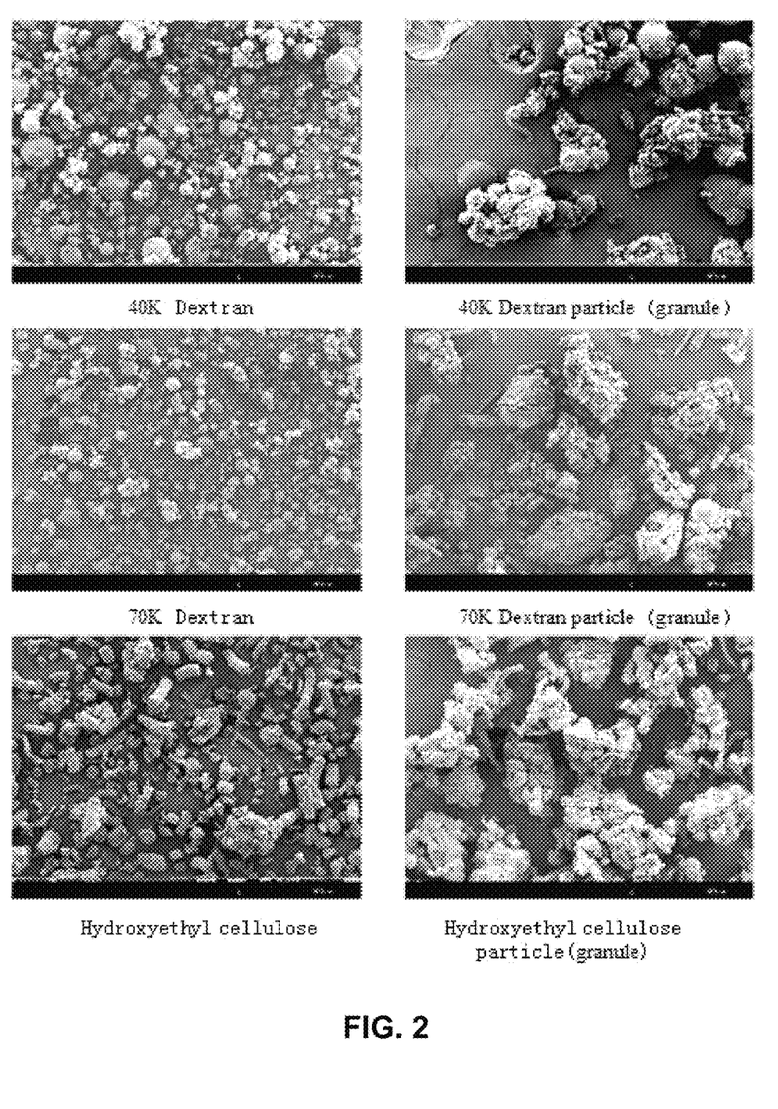
FIG. 2 shows SEM images of microparticles of respective polymers (dextran and hydroxy ethylcellulose) manufactured in the example of the present invention.
Figure 3:
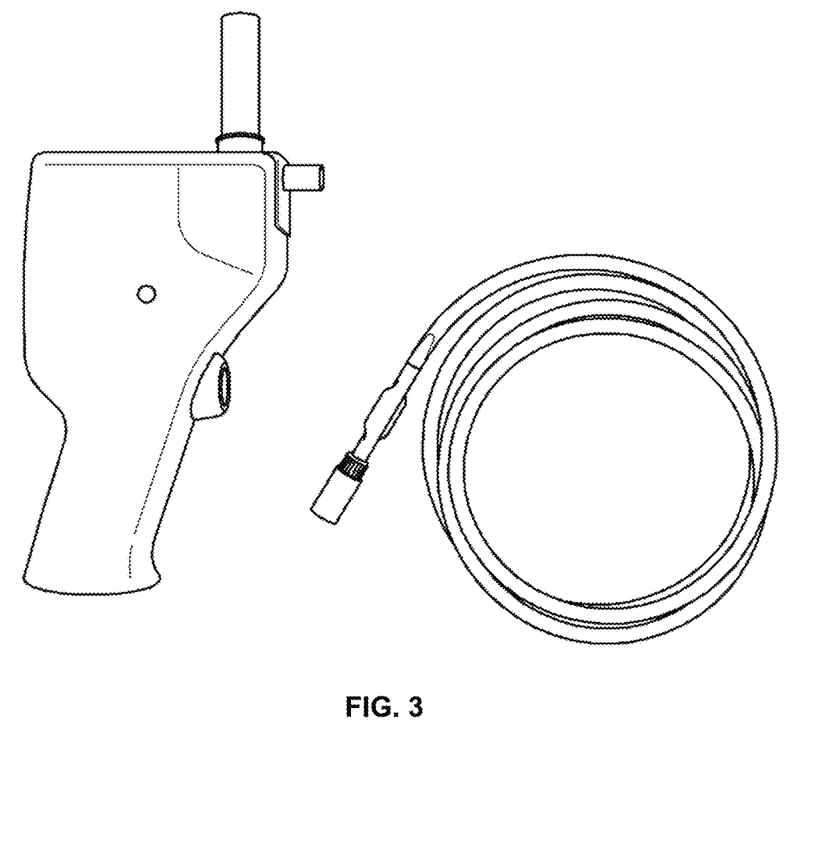
FIG. 3 shows images illustrating actual figures of a spray device body marketed.
Figure 4:
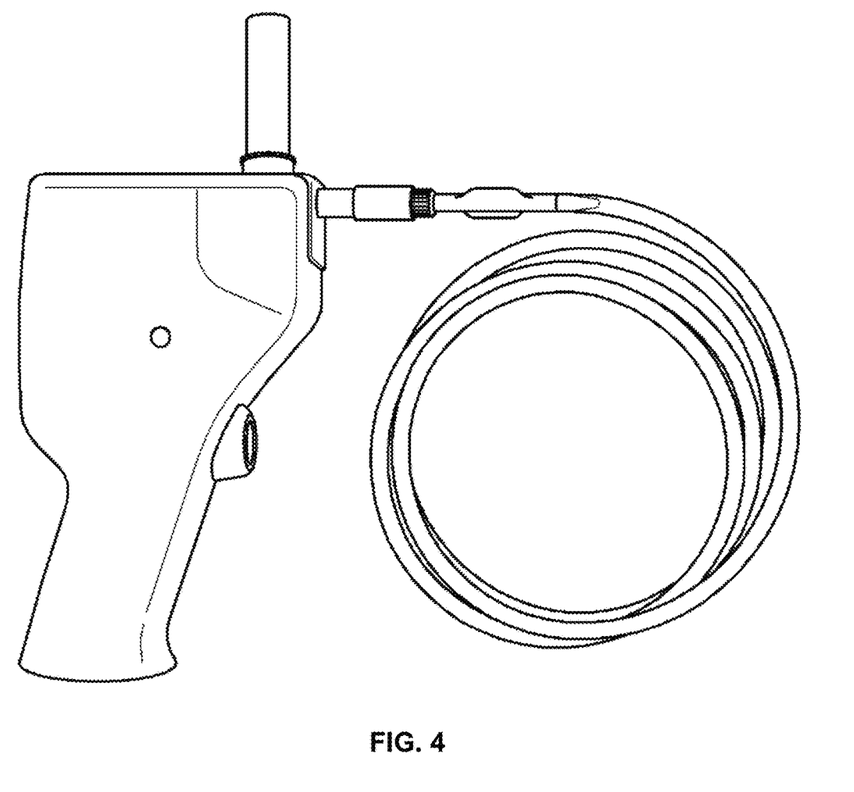

At the time of spraying, the degree of spray was evaluated by checking the residual amount of polymer particles at each site of Alto Shooter. The evaluation basis was set such that the spray power was evaluated to be poor if many polymer particles remain at each site or the blockage occurs, and to be good if few polymer particles remain at each site and the blockage does not occur.

Evaluation results are shown in table 2 below.

<Evaluation Basis>

+++: Few polymer particles remain in the spray device and no blockage occurs.

++: Polymer particles remain in the spray device and no blockage occurs.

+: Polymer particles remain in the spray device and blockage occurs.

TABLE 2

|  | Granule size (μm) | Spray amount | Remaining on bottle | Shooter hole blockage | Connector blockage | Catheter blockage |
|---|---|---|---|---|---|---|
| 40K Dextran | 100-350 | +++ | +++ | +++ | +++ | +++ |
| 70K Dextran | 100-350 | +++ | +++ | +++ | +++ | +++ |
| Hyaluronic acid | 100-350 | +++ | +++ | +++ | +++ | +++ |
| Alginate | 100-350 | +++ | +++ | +++ | +++ | +++ |
| Chitosan | 100-350 | +++ | +++ | +++ | +++ | +++ |
| Hydroxyethyl cellulose (HEC) | 100-350 | +++ | +++ | +++ | +++ | +++ |

As shown in Table 2 above, the polymer particles having a particle diameter of 100-350 μm were excellent in view of the spray power, hardly remained at each site of the spray device, and have no blockage occurred in the conduit (table 2). Meanwhile, the blockage of the conduit occurred in the Hemospray and Endoclot™ (particle size: 100 μm or less), which are currently accessible products.

In addition, the polymer particles were sprayed according to the size (100 μm or less, 100-350 μm, and 350-600 μm) a total of 10 times using Alto Shooter, and then the rate of spray success was calculated. The quantitative results of the recovery rate (%) after spray (or spray amount; equation 1) were evaluated using the spray amount at the time of spray and the remaining amount, and the results are shown in table 3.

$$\text{Spray amount (\%)} = \frac{\text{Sprayed polymer (g)}}{\text{Initial polymer (g)}} \times 100 \quad \text{[Equation 1]}$$

TABLE 3

| Granule size | Rate of spray success | recovery rate after spray |
|---|---|---|
| −100 μm | 10% | 50% |
| 100-350 μm | 100% | 85% |
| 350-600 μm | 0% | 0% |

As shown in table 3 above, the polymer particles having a particle diameter of 100-350 μm had very excellent spray power compared with the particles with the other particle diameters, and caused no blockage in the conduit. Whereas, the particles with a particle diameter of 100 μm or less were not well sprayed since they cause the blockage in the conduit, and the particles with a particle diameter of 350-600 μm were never sprayed (table 3).

Meanwhile, as shown in Table 3, the recovery rate after the spray of the polymer particles with a diameter of 100-350 μm was 85%, and the reason is that, after the spray, the polymer particles do not remain in the vial, but a slight loss of the polymer particles occurs due to static electricity on the wall surfaces of the device and the catheter (Thus, the maximal recovery rate was 80-85%).

Furthermore, the polymer particles (particle diameter of 100-350 μm) were sprayed through conduits with different inner diameters (1.9 Φ, 2.0 Φ, and 2.2 Φ) using Alto Shooter, and then the spray amount thereof was evaluated (equation 2). The results are shown in Table 4.

$$\text{Spray amount (\%)} = \frac{\text{Sprayed polymer (g)}}{\text{Initial polymer (g)}} \times 100 \quad \text{[Equation 2]}$$

TABLE 4

|  | Inner diameter of catheter | | |
|---|---|---|---|
|  | 1.9 Φ | 2.0 Φ | 2.2 Φ |
| Spray amount | 81% | 81% | 82% |

As shown in table 4, the particles with a diameter of 100-350 μm that were confirmed in the conduit with an inner diameter of 1.9-2.2 mm were well sprayed without the blockage in the conduit (table 4).

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A method for endoscopically administering polymer microparticles in vivo through a medical conduit with an inner diameter of 1.0-3.5 mm at a pressure of 0.5-2 bar, wherein the polymer microparticles are granules with a particle diameter of 100-350 μm containing a non-cross-linked biocompatible and biodegradable polymer selected from the group consisting of alginate, chitosan, dextran, polylysine, hyaluronic acid, and hydroxyethylcellulose and a medical excipient.

2. The method of claim 1, wherein the medical excipient is selected from the group of lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxy benzoate, propyl hydroxy benzoate, talc, magnesium stearate and mineral oil.

* * * * *